United States Patent [19]

Noguchi et al.

[11] Patent Number: 5,271,770
[45] Date of Patent: Dec. 21, 1993

[54] PLATELET-LIKE PIGMENTS COATING WITH AN OPTIONAL FIRST LAYER OF BARIUM OR CALCIUM SULFATE AND A LAYER OF TITANIUM AND ZIRCONIUM DIOXIDE, WHICH PREVENT TRANSMISSION OF ULTRAVIOLET AND INFRARED RAYS

[75] Inventors: Tamio Noguchi; Tamio Aikawa, both of Iwaki, Japan

[73] Assignee: Merck Patent Gesellschaft mit beschränkter Haftung, Darmstadt, Fed. Rep. of Germany

[21] Appl. No.: 953,161

[22] Filed: Sep. 29, 1992

Related U.S. Application Data

[63] Continuation of Ser. No. 570,076, Aug. 20, 1990, abandoned.

[51] Int. Cl.⁵ .................... C04B 14/20; C09C 3/06
[52] U.S. Cl. ...................... 106/415; 106/417; 106/418; 106/438; 106/450; 106/459
[58] Field of Search ............. 106/415, 417, 418, 438, 106/450, 459

[56] References Cited

U.S. PATENT DOCUMENTS

| | | | |
|---|---|---|---|
| 3,087,828 | 4/1963 | Linton | 106/417 |
| 3,711,308 | 1/1973 | Brand et al. | 106/418 |
| 3,869,298 | 4/1975 | Suzuki et al. | 106/418 |
| 3,874,890 | 4/1975 | Bernhard et al. | 106/418 |
| 3,926,659 | 12/1975 | Bernhard et al. | 106/417 |
| 4,435,220 | 3/1984 | Watanabe et al. | 106/415 |
| 4,603,047 | 7/1986 | Watanabe et al. | 106/417 |
| 4,956,019 | 9/1990 | Noguchi et al. | 106/415 |

FOREIGN PATENT DOCUMENTS 3221045 8/1983 Fed. Rep. of Germany.

Primary Examiner—Mark L. Bell
Assistant Examiner—Scott L. Hertzog
Attorney, Agent, or Firm—Millen, White, Zelano & Branigan

[57] ABSTRACT

A pigment comprising leaf-like substrates particles having a particle size of 0.5 to 100 μm, whereby the surface of said particles is covered with a metal oxide comprising titanium oxide and zirconium oxide in a molar ratio of 10:1 to 10:15 within a range of from 20 wt. % to 60 wt. % based on the total weight of the pigment possesses good adhesion and spreadability and has an effect of preventing ultraviolet rays and infrared rays.

16 Claims, No Drawings

PLATELET-LIKE PIGMENTS COATING WITH AN OPTIONAL FIRST LAYER OF BARIUM OR CALCIUM SULFATE AND A LAYER OF TITANIUM AND ZIRCONIUM DIOXIDE, WHICH PREVENT TRANSMISSION OF ULTRAVIOLET AND INFRARED RAYS

This is a continuation of application Ser. No. 07/570,076 filed Aug. 20, 1990, now abandoned.

BACKGROUND OF THE INVENTION

The present invention relates to novel pigments which possess good adhesion and spreadability and have the effect of preventing or lessening that transmission of ultraviolet and infrared rays. Ultraviolet and infrared rays are known to cause erythematous response or skin pigmentation in mammals, e.g., humans.

It has been pointed out that when the skin is exposed to ultraviolet rays or infrared rays in the sunlight, skin temperature increases due to infrared rays, whereby the photochemical reaction of ultraviolet rays is accelerated so that so-called sunburn tends to be caused. Furthermore, near infrared rays at 760 nm to 1500 nm can be a factor causing low temperature burn or skin aging changes, accompanied by evaporation of epidermal moisture, so-called photoaging, etc. As cosmetics which have a light-protecting effect, there have been recently provided cosmetic compositions in which UV absorbents of an organic compound type such as quinine sulfate or p-aminobenzoic acid are incorporated or in which the effect of shielding ultraviolet rays at 300 to 400 nm is achieved by utilizing the light scattering effect of inorganic powders, for example, zinc oxide or titanium oxide.

In addition, as powders for simultaneously scattering ultraviolet rays and infrared rays, nylon particles having zirconium oxide bound thereto or aluminum powders treated with titanium oxide have been developed. However, these prior art cosmetics do not have good adhesion or spreadability on the skin and are also unsatisfactory in other desired properties such as smoothness, soft touch, transparency, color hue, etc. and in their ability to prevent transmission of both ultraviolet rays and infrared rays.

Furthermore, organic compounds that prevent transmission of substantial amounts of ultraviolet rays and infrared rays at the same time are unknown, and available compounds are irritating to the skin, and have insufficient stability to light. In particular, reflection of a sufficient amount of near infrared rays at 760 nm to 1500 nm is not achieved by the available organic compounds.

West German Patent No. 32210451A discloses a titanium oxide-covered mica-type pearlescent pigment; in preparing the pigment, a trace amount of zirconium oxide is deposited together with titanium oxide for purposes of improving its luminescence and adhesion of titanium oxide. However, the pigment does not have sufficient infrared ray reflection properties. Furthermore, the luminescence is so strong that it is unsuited as a powder foundation, etc. for use in cosmetics.

In addition, the infrared ray reflection properties of pearlescent pigments having a red interference color which is obtained by covering mica with 50 to 60 wt. % of titanium oxide is reported by Poelman et al. [M.C. Poelman et al., Preprints of the XIVth I.F.S. Congress Barcelona, Vol. II, 749 (1986)]. However, in this pigment in the luminescence is also strong so that the pigment is undesirable for use as a powder foundation.

SUMMARY OF THE INVENTION

As a result of extensive investigations to find pigments having good adhesion and spreadability on the skin, having suitable smoothness, soft touch, transparency, gloss, and hue and having the ability to prevent transmission of ultraviolet and infrared rays, the present inventors have succeeded in providing novel pigments which are obtained by covering a leaf-like (i.e., "platelet-like") substrate with a metal oxide mixture of titanium oxide and zirconium oxide in a suitable ratio.

That is, the present invention provides novel pigments comprising leaf-like substrate particles such as mica, talc, sericite, kaolin, etc. characterized by covering the surface of the particles with a metal oxide comprising titanium oxide and zirconium oxide in a molar ratio of 10:1 to 10:15, said covering being in total within a range of from about 20 wt. % to 60 wt. %, preferably about 30–58%, of metal oxide based on the total weight of the pigment.

The present invention also relates to novel pigments obtained by previously covering the surface of leaf-like substrate particles with barium or calcium sulfate, in an amount effective to improve spreadability, gloss, and adhesion to the skin, and further covering with the aforesaid metal oxide composed of titanium oxide and zirconium oxide, and a process for preparation thereof.

The novel pigments in accordance with the present invention can be prepared as described below:

(1) First, the aforesaid leaf-like substrate particles are suspended in water.

(2) Next, (a) an aqueous solution of a titanium compound and a zirconium compound and (b) an aqueous solution containing an alkaline hydroxide or an alkaline carbonate are added to the suspension, simultaneously or sequentially in the order of (a) and (b), with heating while stirring, thereby to deposit the hydrated titanium oxide and hydrated zirconium oxide onto the surface of the leaf-like substrate particles.

(3) The resulting solid product is separated, dried, and, if necessary, sintered.

The thus-obtained leaf-like substrate particles on which titanium oxide and zirconium oxide have been deposited are extremely excellent in terms of their ability to reflect ultraviolet and infrared rays. Generally, the amount of Uv rays transmitted is less than 10% at a wavelength of 300 nm. The amount of IR rays transmitted is less than 30% at a wavelength of 900 nm.

For purposes of improving spreadability and adhesion to the skin and gloss (luster, brightness) of powders, the present invention also provides novel pigments comprising leaf-like substrate particles obtained by previously covering the surface of the particles with barium or calcium sulfate and further covering the surface of the particles with the aforesaid metal oxide composed of titanium oxide and zirconium oxide. Preferably, barium or calcium sulfate is added so that 10–35 wt. %, more preferably 12–30 wt. % is present on the substrate, based on total pigment weight. In this case, the pigment can be prepared as described below:

(1) The leaf-like substrate particles are suspended in water.

(2) Next, (c) an aqueous solution containing barium or calcium ions and (d) an aqueous solution containing titanium sulfate and a zirconium compound in water is added to the suspension, simultaneously or sequentially in the order of (c) and (d), with heating while stirring, thereby to previously deposit barium or calcium sulfate onto the surface of the leaf-like substrate particles and further adding (b) an aqueous solution containing an alkaline hydroxide or an alkaline carbonate to the mixture, with heating while stirring, thereby depositing barium sulfate, hydrated titanium oxide, and hydrated zirconium oxide onto the surface of the leaf-like substrate particles.

(3) The resulting solid product is separated, dried, and, if necessary, sintered.

The thus-obtained leaf-like substrate particles onto the surface of which barium or calcium sulfate, hydrated titanium oxide, and hydrated zirconium oxide have been deposited with good adhesion to and spreadability on the skin, have suitable smoothness, soft touch, transparency, gloss, and hue and have excellent ability to prevent transmission of ultraviolet and infrared rays.

Examples of titanium compounds usable in the aqueous solution (a) described above include titanium tetrachloride, titanium trichloride, titanyl oxysulfate, etc. Examples of zirconium compounds include zirconium chloride oxide octahydrate, zirconium sulfate, etc. Examples of alkaline oxides in the aqueous solution (b) described above include sodium hydroxide, potassium hydroxide, and ammonium hydroxide. In this case, compounds that form ammonium hydroxide, for example, urea and the like may also be used.

Examples of alkaline carbonates described above include carbonates of alkali metals, such as sodium carbonate, sodium hydrogencarbonate, potassium hydrogencarbonate, ammonium carbonate, ammonium hydrogencarbonate, etc.

Examples of the aqueous solution containing barium or calcium ions in the aqueous solution (c) described above include aqueous solutions of barium or calcium chloride, barium or calcium hydroxide, barium or calcium nitrate, barium or calcium sulfide, etc.

Of these barium and calcium compounds, barium or calcium nitrates are preferred in view of their accessibility, price, purity, etc. Barium compounds are especially preferred.

The particle diameter of the leaf-like substrate particles used in the present invention is about 0.5 to 100 μm, preferably 2 to 50 μm. As the leaf-like substrate, clay minerals, such as mica, talc, sericite, kaolin, etc., are used.

One embodiment of the process for preparing the novel pigments of the present invention is described below.

In 100 parts of water is suspended 5 parts of leaf-like substrate particles. While stirring at 0° to 100° C., preferably 20° to 95° C., an aqueous solution containing 5 to 35 wt. % of the titanium compound is added which contains 0.1 to 1.5 molar equivalents based on the titanium compound. The resulting solution (the aqueous solution (a) described above) is added to 5 to 35 wt. % of a basic aqueous solution (the aqueous solution (b) described above) with stirring, while controlling the pH during the reaction of 1.5 to 2.5. The pH after the reaction is adjusted to the pH at which the metal hydroxide is completely deposited.

After the reaction, the solid product is separated by filtration and washed with water. Then the product is dried at 105° to 110° C. for about 12 hours. In the case where it is desired to convert the metal hydroxide to the oxide, the resulting solid product is sintered at a suitable temperature.

For purposes of improving spreadability and adhesion to the skin and gloss (luster, brightness) of powers, as noted above, the surface of the leaf-like substrate particles may be previously covered with barium sulfate and the metal oxide composed of titanium oxide and zirconium oxide is coated onto the particle surface. One embodiment of this process is described below.

After 5 parts of the leaf-like substrate particles are suspended in 100 parts of water, an aqueous solution containing 5 to 25 wt. % of a barium salt, 1.01 to 2.00 molar equivalents of titanyl sulfate to the barium salt and 0.1 to 1.5 molar equivalents of zirconium compound to the titanyl sulfate is dropwise added to the suspension at 0° to 100° C., preferably 20° to 95° C., while stirring. After completion of the dropwise addition, 5 to 35 wt. % of a basic aqueous solution (the aqueous solution (b) described above) is dropwise added to the mixture and a pH in the aqueous solution is adjusted to 3.0 to 10.0.

After the reaction, the solid product is separated by filtration and washed with water. Then the product is dried at 105° to 100° C. for about 12 hours. In the case where it is desired to convert the metal hydroxide to the oxide, the resulting solid product is sintered at a suitable temperature.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications, if any, cited above and below, and of Japanese Application No. 89-212972, filed Aug. 21, 1989, are hereby incorporated by reference.

EXAMPLES

EXAMPLE 1

After 50 g of talc particles having a particle diameter of 1 to 30 microns is suspended in 1000 ml of water, 50 ml of ethanol is added to the suspension to improve dispersibility of the talc particles in water. While stirring with heating at 70° C., a solution obtained by adding 55 ml of an aqueous solution containing 15 wt. % of zirconium chloride oxide octahydrate to 300 ml of an aqueous solution containing 15 wt. % of titanium tetrachloride is dropwise added to the mixture at a rate of 3 ml/min.

The pH of the suspension is adjusted to 1.5 to 2.5 by adding an aqueous solution containing 15 wt. % of sodium hydroxide thereto. After completion of the dropwise addition, the pH of the suspension is adjusted to 6.5 using an aqueous solution containing 15 wt. % of sodium hydroxide.

The resulting product is separated by filtration and washed with water to remove the salt. Then the product is dried at 105° to 110° C. for 13 hours and sintered at 700° C. for an hour.

The thus-obtained pigment shows good spreadability and adhesion to the skin, excellent dispersibility, and excellent reflection of ultraviolet and infrared rays.

EXAMPLE 2

After 50 g of kaolin having a diameter of 20 microns or less is suspended in 1000 ml of water, a solution obtained by adding 20 ml of an aqueous solution containing 15 wt. % of zirconium chloride oxide octahydrate to 300 ml of an aqueous solution containing 15 wt. % of titanium tetrachloride is dropwise added to the suspension at a rate of 3 ml/min.

The pH of the suspension is adjusted to 1.5 to 2.5 by adding an aqueous solution containing 15 wt. % of sodium hydroxide thereto. After completion of the dropwise addition, the pH of the suspension is adjusted to 6.5 using an aqueous solution containing 15 wt. % of sodium hydroxide.

The resulting product is separated by filtration and washed with water to remove the salt. Then the product is dried at 105° to 110° C. for 13 hours and sintered at 700° C. for an hour.

The thus-obtained white product reflects ultraviolet and infrared rays.

EXAMPLE 3

After 70 g of silk mica particles having a particle diameter of 1 to 40 microns is suspended in 1 liter of water, the mixture is heated to 85° C. While stirring, a solution mixture of 200 g of an aqueous solution containing 34 wt. % of titanyl sulfate and 80 g of an aqueous solution containing 30 wt. % of zirconium chloride oxide octahydrate is dropwise added to the mixture at a rate of 2 ml/min. After completion of the dropwise addition, the pH of the suspension is adjusted to 7.0 while dropwise adding an aqueous solution containing 30 wt. % of sodium hydroxide at a rate of 1.5 ml/min. to the mixture.

The resulting product is separated by filtration and washed with water to remove the salt. Then the product is dried at about 105° to 110° C. for 15 hours and sintered at 700° C. for 40 minutes.

The thus-obtained white product shows excellent reflection of ultraviolet and infrared rays.

EXAMPLE 4

To an aqueous solution of 100.8 g of barium nitrate in 2 liters of water is added 90 mg of white mica particles having a particle diameter of 1 to 15 microns to suspend the particles. The suspension is heated to 80° C. and a solution mixture of 530 g of an aqueous solution containing 34 wt. % of titanyl sulfate and 261.7 g of an aqueous solution containing 30 wt. % of zirconium chloride oxide octahydrate is dropwise added to the suspension at a rate of 5.4 ml/min. After completion of the dropwise addition, the pH of the suspension is adjusted to 7.0 while dropwise adding an aqueous solution containing 30 wt. % of sodium hydroxide at a rate of 3.0 ml/min. to the mixture. The resulting product is precipitated, filtered, and washed with water to remove the salt. Then the product is dried at 105° to 110° C. for 15 hours and sintered at 700° C. for 40 minutes. The thus-obtained product shows extremely excellent reflection of ultraviolet and infrared rays.

EXAMPLE 5

The procedure is conducted in a manner similar to Example 4, except that the amount of barium nitrate, the heating temperature, the amount of the aqueous solution containing 34 wt. % of titanyl sulfate used and the amount of the aqueous solution containing 30 wt. % of zirconium chloride oxide octahydrate are changed to 84 g, 90° C., 41.7 g, and 523 g, respectively, in Example 4. The obtained product shows excellent reflection of ultraviolet and infrared rays.

EXAMPLE 6

The procedure is operated in a manner similar to Example 5, except that the amount of the aqueous solution containing 34 wt. % of titanyl sulfate used and the amount of the aqueous solution containing 30 wt. % of zirconium oxide octahydrate are changed to 353.4 and 653.8 g, respectively, in Example 5. The obtained white product shows extremely excellent reflection of ultraviolet and infrared rays.

EXAMPLE 7

The procedure is operated in a manner similar to Example 4, except that silk mica particles having a particle diameter of 1 to 40 microns are used instead of white mica particles. A white powder showing excellent reflection of ultraviolet and infrared rays is obtained.

EXAMPLE 8

The pigment obtained in each of the examples described above is dispersed in a medium of polyvinyl chloride type having a solid content of 20%. The dispersion is coated onto a glass plate in a wet state using an applicator having a thickness of 120 μm. After drying, a membrane is obtained. Using the membrane, the ultraviolet region (400 to 260 nm) and the near infrared region (760 to 900 nm) are measured with a double beam spectrophotometer Model 228 (manufactured by Hitachi Ltd.). The light transmission at wavelengths of 300 nm and 900 nm is less than 10% and less than 30%, respectively.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the reduction of the transmission of ultraviolet or infrared radiation into a surface, comprising coating said surface with a pigment comprising a platelet-like substrate particle having a surface covered with a metal oxide mixture consisting essentially of titanium oxide and zirconium oxide in a molar ratio of about 10:1 to 10:15, in a amount of about 20 wt. % to 60 wt. % based on the total weight of the pigment.

2. A method of claim 1, wherein the surface of said platelet-like substrate particles is coated with barium or calcium sulfate prior to coating with titanium oxide and zirconium oxide.

3. A method of claim 1, wherein the surface of said platelet-like substrate particles is coated with barium sulfate prior to coating with titanium oxide and zirconium oxide.

4. A method of claim 1, wherein the diameter of the substrate is about 0.5 to 100 μm.

5. A method of claim 1, wherein the diameter of the substrate is about 2 to 5 μm.

6. A method of claim 1, wherein the substrate is mica, talc, sericite, or kaolin.

7. A method of claim 1, wherein less than about 10% of impinging ultraviolet and less than about 30% of impinging infrared rays are transmitted through said pigment.

8. A method according to claim 1, wherein the surface is the skin of a mammal.

9. A method according to claim 1, wherein the pigment contains 18-231.3% by weight zirconium oxide with respect to the weight percent of titanium dioxide.

10. A method according to claim 1, wherein the pigment contains 25-231.3% by weight zirconium oxide with respect to the weight percent of titanium dioxide.

11. A method according to claim 1, wherein the pigment contains 30-231.3% by weight zirconium oxide with respect to the weight percent of titanium dioxide.

12. A method according to claim 1, wherein the pigment contains 35-231.3% by weight zirconium oxide with respect to the weight percent of titanium dioxide.

13. A method according to claim 1, wherein the pigment contains 50-231.3% by weight zirconium oxide with respect to the weight percent of titanium dioxide.

14. A method according to claim 1, wherein the pigment contains 100-231.3% by weight zirconium oxide with respect to the weight percent of titanium dioxide.

15. A method according to claim 1, wherein the pigment contains 200-231.3% by weight zirconium oxide with respect to the weight percent of titanium dioxide.

16. A method for achieving an improved reduction of the transmission of ultraviolet or infrared rays onto a surface compared to that achieved by coating with conventional zirconium and titanium dioxide containing pigments, comprising coating said surface with a platelet-like substrate particle having a surface covered with a metal oxide mixture consisting essentially of titanium oxide and zirconium oxide in a molar ratio of about 10:1 to 10:15, in a amount of about 20 wt. % to 60 wt. % based on the total weight of the pigment.

* * * * *

UNITED STATES PATENT AND TRADEMARK OFFICE
CERTIFICATE OF CORRECTION

PATENT NO. : 5,271,770
DATED : December 21, 1993
INVENTOR(S) : Tamio NOGUCHI et al.

It is certified that error appears in the above-identified patent and that said Letters Patent is hereby corrected as shown below:

Title Page:

Item [30] add the following: --Foreign Application Priority Data
                Aug. 21, 1989 (JP) Japan   89-212972--

Signed and Sealed this

Fifth Day of July, 1994

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,271,770
DATED : December 21, 1993
INVENTOR(S) : Tamio NOGUCHI et al.

It is certified that error appears in the above-indentified patent and that said Letters Patent is hereby corrected as shown below:

Title Page: Item (75), Inventors:

Delete the second inventor's first name and replace with - - Masahiro - - .

Signed and Sealed this

Twenty-second Day of August, 1995

Attest:

BRUCE LEHMAN

Attesting Officer

Commissioner of Patents and Trademarks